United States Patent [19]

Fuller et al.

[11] Patent Number: 4,822,997

[45] Date of Patent: Apr. 18, 1989

[54] APPARATUS FOR AND METHOD OF MEASURING AND/OR CONTROLLING THE USE OF FIBER OPTIC CONDUCTORS

[75] Inventors: Terry A. Fuller, Highland Park; Anish A. Ukani, Wheeling, both of Ill.

[73] Assignee: Fullen Research Corporation, Vernon Hills, Ill.

[21] Appl. No.: 117,119

[22] Filed: Nov. 4, 1987

[51] Int. Cl.⁴ .............................................. H01J 5/16
[52] U.S. Cl. .................................... 250/227; 356/73.1
[58] Field of Search ............................ 250/227, 205; 219/121 L, 121 LM, 121 LZ; 128/303.1, 395, 398; 356/73.1

[56] References Cited

U.S. PATENT DOCUMENTS

| | | | |
|---|---|---|---|
| 3,642,007 | 2/1972 | Roberts et al. | 128/303.1 |
| 4,268,818 | 5/1981 | Davis et al. | 340/870.38 |
| 4,657,013 | 4/1987 | Hoerenz et al. | 128/303.1 |

Primary Examiner—David C. Nelms
Attorney, Agent, or Firm—Seidel, Gonda, Lavorgna & Monaco

[57] ABSTRACT

An apparatus for determining the usage of an optical conductor. The apparatus comprises a non-volatile memory operatively associated with the conductor for storing a cumulative usage value representative of the cumulative usage of the conductor. A device responsive to a parameter of use generates a signal representative of usage of the conductor. A circuit is provided which is responsive to the signal and is operatively associated with the memory for generating from the signal a usage value and then generating from the usage value and cumulative usage value stored in the memory an updated cumulative usage value representative of the total cumulative usage of the conductor, and for replacing the cumulative usage value in the memory with the updated cumulative usage value. The circuit may in addition compare the cumulative usage value to a predetermined value representative of maximum usage. Structure operatively associated with the circuit is provided for preventing further use of the conductor when the updated cumulative usage value reaches the predetermined value.

27 Claims, 3 Drawing Sheets

APPARATUS FOR AND METHOD OF MEASURING AND/OR CONTROLLING THE USE OF FIBER OPTIC CONDUCTORS

BACKGROUND OF THE INVENTION

Certain fiber optic materials have been shown to have an energy sensitivity. Some fiber optic materials such as KRS-5 decrease their transmissivity with time. The rate of this degradation is accelerated by transmission of radiant energy in the mid-infrared band. Thus, it is desirable, or in some cases necessary (laser surgery, for example), to limit the energy entering or exiting the fiber to prohibit radiant energy destruction of the fiber itself.

In other instances, it is desirable to limit the total energy transmitted through a fiber to limit distal-end degradation. Such is the case in laser surgery using silica-based optical fibers, where the silica-based fiber is destroyed due to contact with the vaporizing tissue. Continued delivery of radiant energy in such cases will result in breaking the fiber and leaving sections of fiber in the patient.

In still other instances, where fibers have windows and/or contact delivery probes, maximum energy limits can prevent failure modes in these structures.

In addition, in some cases optical fibers can become degraded or damaged as a result of mechanical stresses (e.g., bending, flexing, accidental dropping, etc.) incident to their use. It may be necessary or desirable to limit the total number of uses of an optical fiber to prevent failure due to mechanical causes independent of the energy exposure of the fiber.

Accordingly, there is a need for a device which will keep an accumulated record of the usage of an optical fiber, and in addition is able to control and limit use of the fiber as desired. It is also desirable that the accumulated usage history of a fiber travel with the fiber upon disconnection and reconnection of the fiber.

SUMMARY OF THE INVENTION

The present invention is an apparatus for determining the usage of an optical conductor and comprises non-volatile memory means operatively associated with the conductor for storing a cumulative usage value representative of cumulative usage of the conductor. Means are provided for generating a signal representative of usage of the conductor. Circuit means are provided responsive to the signal and operatively associated with the memory means for generating from the signal a usage value and for generating from the usage value and the cumulative usage value an updated cumulative usage value representative of the total cumulative usage of the conductor and replacing the cumulative usage value already in the memory means with the updated cumulative usage value.

The apparatus may also include comparison circuit means for comparing the updated cumulative usage value to a predetermined value representative of maximum permitted usage, and means operatively associated with the comparison circuit means may be provided for preventing further use of the conductor when the updated cumulative usage value reaches the predetermined value.

The invention can thus be used either to measure total cumulative usage without performing a control function or to perform both measurement and control.

DESCRIPTION OF THE DRAWINGS

For the purpose of illustrating the invention, there is shown in the drawings a form which is presently preferred; it being understood, however, that this invention is not limited to the precise arrangements and instrumentalities shown.

DESCRIPTION OF THE INVENTION

Figures 1, 2:
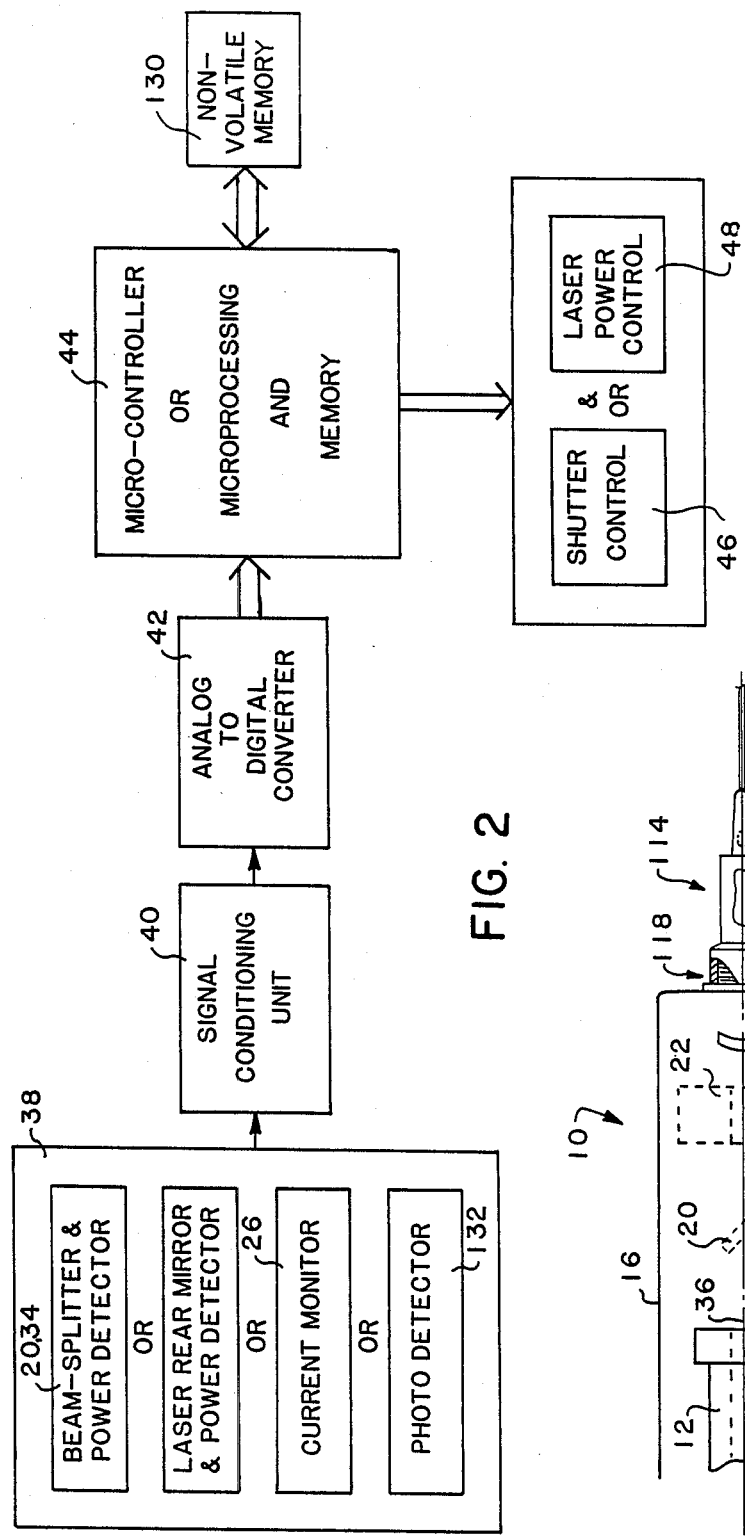
FIG. 1 is a simplified illustration of an integrated optical system employing the present invention.
FIG. 2 is a simplified block diagram illustrating the present invention.

Referring now to the drawings, wherein like numerals indicate like elements, there is shown in FIG. 1 an integrated optical system 10 in accordance with the present invention. Optical system 10 comprises a source of radiant power such as laser 12 and a fiber optic cable assembly 114. Laser 12 is located in a housing 16, along with certain other components to be described later. (The system 10 of FIG. 1 is referred to as integrated since all of the components except fiber optic cable assembly 114 are contained within single housing 16.) Laser 12 may be any type of laser. Housing 16 is provided with an electro-optical connector 118, by means of which fiber optic cable assembly 114 is connected to housing 16. As shown in FIG. 1, the male mating half of 118a of connector 118 is mounted on housing 16 while fiber optic cable assembly 114 carries the female mating half of 118b of connector 118. However, the opposite arrangement of mating halves can obviously be utilized, as can any other connector configuration.

Within housing 16 and in optical alignment with laser 12 is a focusing lens. Also shown schematically in FIG. 1 is a wire or conductor 26 which supplies operating current to laser 12. At the rear of laser 12 is a power detector (not shown in FIG. 1). The power detector is also conventional with many lasers and well understood, and need not be described in detail. The power detector is arranged to detect power from the rear mirror of the laser, in well-known manner.

As an alternative to utilizing the conventional power detection technique discussed in the preceding paragraph, a beam splitter in optical alignment with laser 12 and power detector 34 may be provided within housing 16 to measure the power in beam 36 from laser 12. Beam splitter 20 and power detector 34 thus form a means for sampling the power output from laser 12 and, therefore, the power being input into fiber optic cable assembly 114. A shutter 22 can be used to control laser emission. The beam splitter, shutter and power detector are conventional and well-understood by those skilled in the art and, accordingly, need not be described in detail here.

Referring to fiber optic cable assembly 114, it comprises a conventional optical conductor 128 which may, for example, be a material such as cladded KRS-5, silica or other suitable optical material. Optical conductor 128 conducts radiant power from laser 12 to a point of use. Included within fiber optic cable assembly 114 is a non-volatile memory 130, which may be any suitable non-volatile memory. Memory 130 may be conveniently housed within mating half 118b of connector 118, so that the memory 130 travels with the fiber optic cable assembly 114 upon disconnection and reconnection of cable assembly 114 to either housing 16 or a similar device. Fiber optic cable assembly 114 may also include a detector 132 arranged to detect power traveling down optical conductor 128, as will be explained more fully below.

Referring now to FIG. 2, there is shown a simplified block diagram of the circuitry of the present invention. The circuitry (with the exception of non-volatile memory 130) may conveniently be contained within housing 16, shown in FIG. 1, or may be packaged separately. In either case, connections among the circuit components and non-volatile memory 130 are preferably made through electro-optical connector 118.

Block 38 in FIG. 2 represents an input to the circuitry, and represents the measurement of radiant power to fiber optic cable assembly 114. Measurement of radiant power input can be accomplished in several ways, and four are illustrated in FIG. 2.

The first three ways are external to fiber optic cable assembly 114. An electronic signal is generated which is representative of the instantaneous value of the radiant power by either the beam splitter 20/power detector 34 combination, the laser rear mirror and an associated power detector, or by monitoring the calibrated electric current supplying laser 12. The amplitude of the calibrated electric supply current is representative of the radiant power output of laser 12, as is well-known in the art. The fourth way of measuring radiant power is with detector 132 located adjacent to optical conductor 128 and within or just outside the protective sheath of fiber optic cable assembly 114 for detecting a signal from the scattered power traveling down the optical conductor 128. This scattered power is representative of incoming radiant power to optical conductor 128. Thus, incoming radiant power to optical conductor 128 is measured indirectly by detector 132 by capturing scattered radiant power from optical conductor 128 or from the incident beam.

The signal from the power detector block 38 is suitably conditioned in signal conditioning unit 40 and then sent to analog-to-digital converter 42, where it is converted from an analog signal to a digital signal. From there, the now-digitized signal is sent to microprocessor and memory circuit 44.

Memory in circuit 44 is suitably programmed for the microprocessor to make real-time calculations of energy being supplied to optical conductor 128 based on the signal from power detector box 38. The real-time calculations are made for each predetermined interval of time during which energy is being supplied to fiber optic cable assembly 114. In operation, at the beginning of each interval, the microprocessor interrogates non-volatile memory 130 and stores in its own data memory the cumulative energy value previously stored in non-volatile memory 130 during the previous exposure interval. (Of course, if optical conductor 128 has not previously been exposed to any energy, the cumulative energy value will be zero.) The microprocessor then performs the real-time calculations of energy being supplied to fiber optic cable assembly 114 based on the signals from the power detector employed. The energy is then calculated for a given interval by the microprocessor according to the relation $$\text{energy} = (\text{power} \times \text{time})$$

and the calculated energy value is then added to the cumulative energy value previously retrieved from non-volatile memory 130, and an updated cumulative energy value is determined. This updated cumulative energy value, which is a part of the cumulative usage to which optical conductor 128 has been exposed during the given exposure interval and all preceding exposure intervals, is read out of the microprocessor and stored in non-volatile memory 130 at the end of the pre-determined exposure interval, and the previous cumulative energy value stored in non-volatile memory 130 is erased.

In addition to storing the cumulative energy exposure of fiber optic cable assembly 114, a maximum cumulative energy exposure value can also be stored in non-volatile memory 130. This permits the microprocessor to constantly compare the current cumulative energy exposure of fiber optic cable assembly 114 with the maximum cumulative energy exposure value and to provide quantitative or qualitative warning or control signals in response to the comparison. For example, memory in circuit 44 can be programmed for the microprocessor to take appropriate action when the maximum cumulative energy value is reached to terminate the incoming energy to fiber optic cable assembly 114, such as closing shutter 22 via shutter control 46 or controlling laser output by a laser power control 48, such as for example interrupting laser supply current 26 to terminate the radiation of power by laser 12.

Non-volatile memory 130 may also be preloaded with other pertinent data, such as a unique fiber serial number, initial transmissivity value of the fiber, date of manufacture, conditions of manufacture and lot numbers of raw materials used to manufacture the fiber. The value of such additional data, and how it can be retrieved and processed, will be readily apparent to those skilled in the art.

Of course, the ways in which memory in circuit 44 can be programmed to perform the operations described above, and the necessary command and control interfaces, are within the level of skill in the art and need not be described in detail here.

In a broader aspect of the invention, non-volatile memory 130 and the microprocessor may also be arranged to determine the total cumulative usage of an optical fiber based on parameters other than or in addition to energy exposure. For example, it may be desirable in certain cases to limit the number of times a fiber optic cable assembly is used or to limit the number of hours it is used, even if the fiber has not yet reached a maximum allowable energy exposure after a predetemined number of uses or hours of use. In that case, detector 132 may be used to generate a signal, as described above, but which is processed in the microprocessor to generate not an energy value but a value representative of a use of fiber optic cable assembly 114 rather than energy exposure of fiber optic cable assembly 114. This signal can be referred to as an event signal. The amount or duration of energy exposure sufficient to be counted as an event can be easily preprogrammed into memory. For example, an event may be the connection of fiber optic cable assembly to housing 16, or may be the connection plus a minimum energy exposure, or connection plus a minimum level of power exposure, or a combination of the three. Disconnection of electro-optical connector 118, turning off the system or zero energy input for a preselected time, can constitute the end of an event. The event signal is transformed into an event value by the microprocessor and then accumulated as a cumulative event value.

As with the previously described embodiment, at the beginning of each event, the microprocessor interrogates non-volatile memory 130 and stores in its own data memory the cumulative event value previously stored in non-volatile memory 130 during the previous use. (Of course, if fiber optic cable assembly has not previously been used, the cumulative event value will be zero.) The event value is then added to the cumulative event value previously retrieved from non-volatile memory 130, and an updated cumulative event value is determined. This updated cumulative event value, which is part of the total cumulative usage of optical conductor 128, is read out of memory in circuit 44 and stored in non-volatile memory 130 at the end of the determined event, and the previous cumulative event value stored in non-volatile memory 130 is erased.

In addition to storing the cumulative event value of fiber optic cable assembly 114, a maximum cumulative event value can also be stored in non-volatile memory 130. This permits memory in circuit 44 to be suitably programmed for microprocessor to constantly compare the cumulative event value of fiber optic cable assembly 114 with the maximum cumulative event value and to provide quantitative or qualitative warning or control signals in response to the comparison. For example, memory in circuit 44 can be programmed for the microprocessor to take appropriate action when the maximum cumulative event value is reached to terminate the incoming power to cable assembly 114, such as closing shutter 22 via shutter control 46, or controlling laser output by, for example, interrupting laser supply current 26 to terminate the radiation of power by laser 12.

It should be understood that the memory in circuit 44 can also be programmed so that incoming power to optical conductor 128 may be terminated, selectably, in response to cumulative energy exposure only, cumulative event value only, or a combination of the two, such as whichever of the maximum cumulative energy value or maximum cumulative event value is reached first. In such case, the microprocessor may generate a usage value which is a function of both the energy value and the event value already described. Thus, if the operator chooses to control usage based on energy exposure only, the event value can be set to zero, whereas if he chooses to control usage based on events only, the energy value can be set to zero. If he chooses to control usage based on the earlier reached of maximum energy exposure or maximum number of events, the invention can be so programmed.

In all of the embodiments described, non-volatile memory may also be pre-loaded with a value representative of maximum power rating of its associated optical conductor 128. In such a case, memory in circuit 44 can be programmed for microprocessor to constantly compare the power being supplied to fiber optic cable assembly 114 with the maximum rated power in real time and to terminate the incoming power if the maximum rated power is exceeded.

Figure 3:
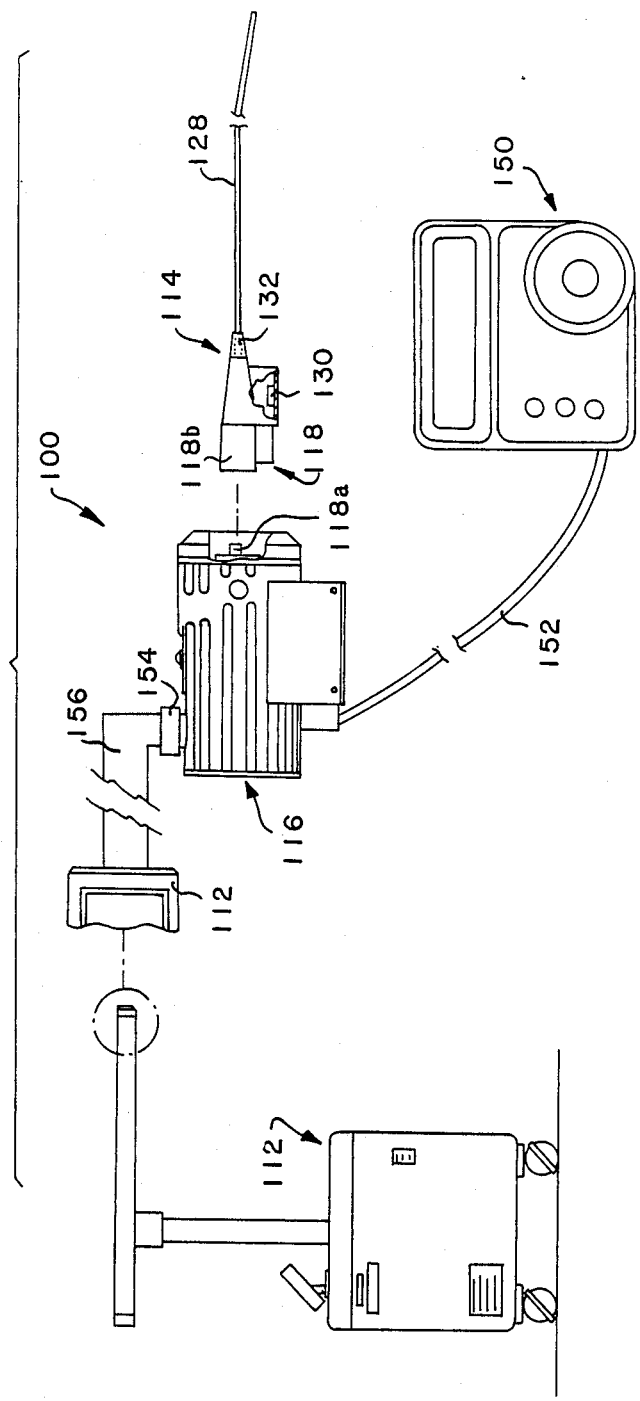
FIG. 3 is a simplified illustration of a non-integrated optical system employing the present invention.
Figure 4:
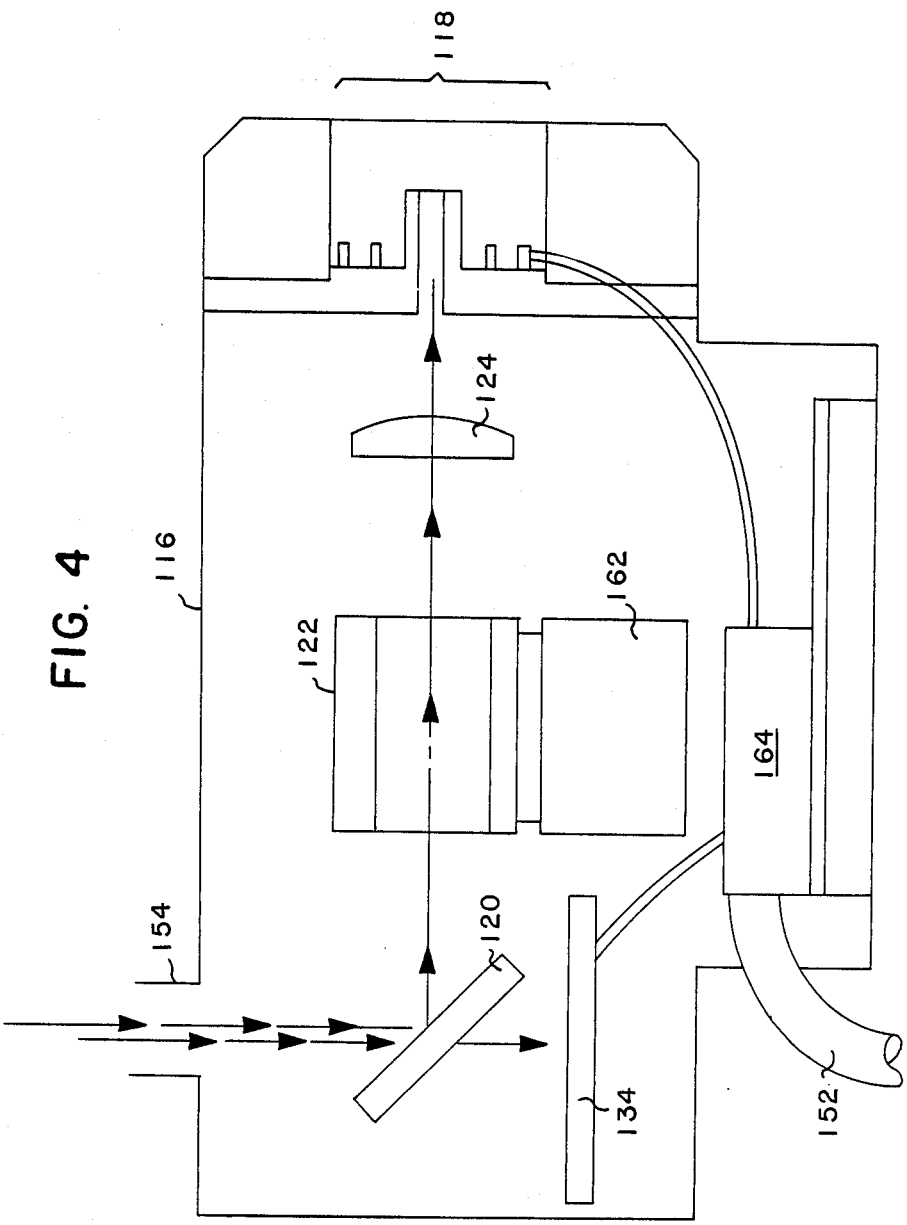
FIG. 4 is a simplified sectional view of the non-integrated optical system component of the system of FIG. 3.

As has already been noted, the embodiment described above is an "integrated" embodiment in that all of the components of the optical systems according to the invention are contained in a single housing, with the exception of fiber optic cable assembly 114. However, the present invention is equally adapted to be utilized with a conventional laser as an "add on" or retrofit system. A preferred embodiment of such a latter system is shown in FIGS. 3 and 4. Referring now to FIG. 3, there is shown an "add on" optical system 100 in accordance with the present invention. Optical system 100 is adapted to be connected between a source of radiant power such as laser 112 and a fiber optic cable assembly 114. As with the first embodiment, laser 112 may be any type of laser. The optical components of system 100 are contained within a housing 116, and the electronic components (the signal conditioning unit, analog-to-digital converter, microprocessor and shutter control electronics) are contained in a control unit 150. Control unit 150 is connected to housing 116 by an electrical cable assembly 152, which carries electrical signals between housing 116 and control unit 150. Alternatively, all or part of the electronic components may instead be contained in housing 116. The electronic components contained in control unit 150 are essentially the same as the electronic components described in connection with the first embodiment, and accordingly are not described further in connection with the second embodiment. That is, all of the electronics described above, and their operation and function, are the same.

Housing 116 is provided with an electro-optical connector 118a, by means of which fiber optic cable assembly 114 is connected to housing 116. As seen in FIG. 3, the male mating half 118a of the electro-optical connector is mounted on housing 116 while fiber optic cable assembly 114 carries the female mating half 118b of the connector. However, as with the first embodiment, the opposite arrangement of mating halves can obviously be utilized, as can any other connector configuration.

Laser 112 is connected to the input 154 of housing 116 by an optical conductor 156, which may be any suitable optical conductor, such as an articulated arm. This permits optical system 100 of the present invention to be used with any laser.

Referring now to FIG. 4, there is shown in sectional view the interior details of housing 116, illustrating the optical components and their placement and operation. Radiation from laser 112, indicated by the dual arrows, enters housing 116 through input 154 and strikes beam splitter 120. A major portion of the light is reflected to the right, as seen in FIG. 4, and is indicated by a single arrow pointing toward the right. The remainder of the radiation passes through beam splitter 120, as indicated by the single arrow pointing downwardly in FIG. 4. The portion of the light which passes through beam splitter 120 strikes detector 134 to measure the power in the beam from laser 112. Thus, as with the first embodiment, beam splitter 120 and power detector 134 form a means for sampling the power output from laser 112, and, therefore, the power being input into fiber optic cable assembly 114.

The portion of the radiation from 112 reflected by the beam splitter 120 passes through tube shutter 122. The shutter 122 is arranged to rotate by means of rotary solenoid 162 located below tube shutter 122.

Also, on the optical axis of housing 116 is a focusing lens 124 which focuses the energy to a beam of diameter small enough to enter the optical conductor 128 of fiber optic cable assembly 114 held in position by electro-optic connector 118.

Necessary electrical connections are made between the various electronic components via electronic components via electronics module 164.

Although omitted for clarity from FIGS. 3 and 4, it is understood that electro-optic connector 118a makes electrical contact with non-volatile memory 130 and detector 132 in fiber optic cable assembly 114. Non-volatile memory 130 and detector 132 are the same as, and perform the same function as, non-volatile memory 130 and detector 132 described in connection with the first embodiment. Internal wiring (also not shown) in housing 116 connect non-volatile memory 130 and detector 132 to control unit via electrical cable assembly 152. Likewise, cable 152 also carries control signals to rotary solenoid 162.

In operation, an electronic signal is generated by the beam splitter 120/power detector 134 combination which is representative of the instantaneous value of the radiant power. Alternatively, as with the first embodiment, radiant power may be measure with photodetector 132 located adjacent to optical conductor 128 and within or just outside the protective sheath of fiber optic cable assembly 114 for detecting a signal from the scattered power traveling down the optical conductor 128.

The detected power signal is then suitably conditioned in a signal conditioning unit (such as signal conditioning unit 40 of FIG. 2) and then sent to an analog-to-digital converter where it is converted from an analog signal to a digital signal. From there, the now-digitized signal is sent to a microprocessor and memory circuit, such as microprocessor and memory circuit 44 of FIG. 2. As with the embodiment of the "integrated" system, the memory is suitably programmed for the microprocessor to make real-time calculations of energy being supplied to the optical conductor 128 or event value of optical conductor 128 or combination of the two. Microprocessor operation is as described in the connection with the first embodiment.

When the microprocessor has determined that the maximum cumulative usage value for fiber optic cable assembly 114 has been reached, it may generate a control signal to rotary solenoid 162. Rotary solenoid 162 causes tube shutter 122 to rotate so that the tube shutter is now interposed in the path of the beam reflected from beam splitter 120. Thus tube shutter 122 effectively blocks the input of further power to fiber optic cable assembly 114 and prevents further use of the fiber optic cable assembly 114. Naturally, any other suitable shutter and shutter control mechanism can be used.

The present invention may be embodied in other specific forms without departing from the spirit or essential attributes thereof and, accordingly, reference should be made to the appended claims, rather than to the foregoing specification, as indicating the scope of the invention.

We claim:

1. Apparatus for determining the usage of an optical conductor, comprising:
    means for generating a signal representative of usage of the conductor,
    non-volatile memory means operatively associated with the conductor for storing a cumulative usage value representative of cumulative usage of the conductor,
    circuit means responsive to the signal and operatively associated with the memory means for generating from the signal a usage value and for generating from the usage value and the cumulative usage value an updated cumulative usage value representative of the total cumulative usage of the conductor, and for replacing the cumulative usage value in the memory means with the updated cumulative usage value.

2. Apparatus according to claim 1, further comprising:
    comparison circuit means for comparing the updated cumulative usage value to a predetermined value representative of maximum permitted usage, and
    control means operatively associated with the comparison circuit means for preventing further use of the conductor when the updated cumulative usage value reaches the predetermined value.

3. Apparatus according to claims 1 or 2, wherein the means for generating the signal is responsive to energy supplied to the optical conductor.

4. Apparatus according to claims 1 or 2, wherein the means for generating the signal is responsive to connection of the conductor to a source of radiant power.

5. Apparatus according to claims 1 or 2, wherein the means for generating the signal is responsive to a preselected one of connection of the conductor to a source of radiant power, connection plus a minimum energy exposure of the conductor, connection plus a minimum power exposure of the conductor, and combinations thereof.

6. Apparatus according to claim 4, wherein the means for generating the signal is programmable.

7. Apparatus for measuring the total cumulative usage of an optical conductor between a state of zero usage and a state of maximum cumulative usage, comprising:
    non-volatile memory means operatively associated with the conductor for storing a cumulative usage value representative of the cumulative usage of the conductor prior to a given use,
    sensor means responsive to a parameter of use of the conductor for generating a signal representative thereof,
    circuit means responsive to the signal and operatively associated with the memory means for generating from the signal a current usage value and for generating from the current usage value and the cumulative usage value an updated cumulative usage value representative of the total cumulative usage of the conductor and replacing the cumulative usage value in the memory means with the updated cumulative usage value.

8. Apparatus according to claim 7, further comprising:
    comparison circuit means for comparing the updated cumulative usage value to a predetermined value representative of maximum cumulative usage, and
    control means operatively associated with the comparison circuit means for preventing further use of the conductor when the updated cumulative usage value reaches the predetermined value.

9. Apparatus for measuring the total cumulative usage of an optical conductor between a state of zero usage and a state of maximum cumulative usage, comprising:
    a source of radiant power,
    sensor means responsive to a parameter of use of the conductor for generating a signal representative thereof,
    non-volatile memory means operatively associated with the conductor for storing a cumulative usage value representative of the cumulative usage of the conductor prior to a given use,
    circuit means responsive to the signal and operatively associated with the memory means for generating from the signal a current usage value and for generating from the current usage value and the cumulative usage value an updated cumulative usage value representative of the total cumulative usage of the conductor and replacing the cumulative usage value in the memory means with the updated cumulative usage value.

10. Apparatus according to claim 9, further comprising:
   comparison circuit means for comparing the updated cumulative usage value to a predetermined value representative of maximum cumulative usage, and
   control means operatively associated with the comparison circuit means and the source of radiant power for terminating the input of said power to the conductor once the updated cumulative usage value reaches the predetermined value.

11. Apparatus according to claims 9 or 10, wherein the source of radiant energy comprises a laser.

12. Apparatus according to claims 9 or 10, wherein the sensor means comprises means for generating a signal representative of the radiant power input to the conductor.

13. Apparatus according to claims 9 or 10, wherein the sensor means comprises a detector operatively associated with the conductor.

14. Apparatus according to claims 9 or 10, wherein the control means comprises a shutter arranged to interrupt the radiant power being input to the conductor.

15. Apparatus according to claim 11, wherein the control means comprises means for terminating the electric current input to the laser.

16. Apparatus for selectably measuring and controlling the total cumulative usage of an optical conductor between a state of zero usage and a state of maximum cumulative usage, comprising:
   a fiber optic cable assembly including an optical conductor and an electro-optic connector at one end thereof,
   a source of radiant power having an electro-optic connector for mating with the connector of the fiber optic cable assembly for coupling the radiant power to the optical conductor,
   non-volatile memory means disposed within the fiber optic cable assembly for storing a cumulative usage value representative of the cumulative usage of the optical conductor prior to a given use, the memory means being in electrical communication with the fiber optic cable connector,
   sensor means responsive to a parameter of use of the optical conductor for generating a signal representative thereof,
   circuit means in electrical communication with the electro-optic connector and responsive to the signal and operatively associated with the memory means for generating from the signal a current usage value and generating from the current usage value and the cumulative usage value an updated cumulative usage value representative of the total cumulative usage of the optical conductor and replacing the cumulative usage value in the memory means with the updated cumulative usage value,
   the circuit means including comparison circuit means for comparing the updated cumulated usage value to a predetermined value representative of maximum cumulative usage, and
   control means operatively associated with the comparison circuit means and the source of radiant power for terminating the input of said power to the optical conductor once the updated cumulative usage value reaches the predetermined value.

17. Apparatus according to claim 16, wherein the sensor means comprises means for generating a signal representative of the radiant power input to the optical conductor.

18. Apparatus according to claim 16, wherein the source of radiant power comprises a laser and the sensor means comprises means for generating a signal representative of the laser power output.

19. Apparatus according to claim 18, wherein the control means comprises a shutter arranged to interrupt the laser output.

20. Apparatus according to claim 18, wherein the control means comprises means for disabling the laser.

21. Apparatus according to claims 2, 8, 10 or 16, further comprising:
   the sensor means being responsive to the power input to the optical conductor and generating a power signal representative of the value of the power,
   the non-volatile memory means being preloaded with a value representative of the maximum power rating of its associated optical conductor,
   said comparison circuit means including means responsive to the sensor means for comparing the sensed power with the maximum power rating stored in the memory means, and
   said control means including means for preventing further use of the conductor whenever the sensed power exceeds the maximum power rating.

22. Apparatus according to claims 1, 2, 7, 8, 9, 10 or 16, further comprising:
   said non-volatile memory being preloaded with data representative of at least one characteristic of the optical conductor.

23. Apparatus according to claim 22, wherein said characteristic comprises an initial transmissivity value of said optical conductor.

24. Apparatus for detecting input optical power supplied to an optical conductor, comprising an optical detector located adjacent an optical conductor for detecting scattered optical power from the conductor and generating a signal representative of the input optical power.

25. Method of determining the usage of an optical conductor, comprising the steps of:
   generating a signal representative of usage of the conductor,
   storing with the conductor a cumulative usage value representative of cumulative usage of the conductor,
   generating from the signal a usage value,
   generating from the usage value and the cumulative usage value an updated cumulative usage value representative of the total cumulative usage of the conductor, and
   replacing the cumulative usage value stored with the conductor with the updated cumulative usage value.

26. Method according to claim 25, further comprising the steps of:
   comparing the updated cumulative usage value to a predetermined value representative of maximum permitted usage, and
   preventing further use of the conductor when the updated cumulative usage value reaches the predetermined value.

27. Method of measuring the total cumulative usage of an optical conductor between a state of zero usage and a state of maximum cumulative usage, comprising the steps of:

storing with the conductor a cumulative usage value representative of the cumulative usage of the conductor prior to a given use, sensing a parameter of use of the conductor and generating a signal representative thereof, generating from the signal a current usage value, generating from the current usage value and the cumulative usage value an updated cumulative usage value representative of the total cumulative usage of the conductor and replacing the cumulative usage value stored with the conductor with the updated cumulative usage value, comparing the updated cumulated usage value to a predetermined value representative of maximum cumulative usage, and preventing further use of the conductor once the updated cumulative usage value reaches the predetermined value.

* * * * *